US006716231B1

(12) United States Patent
Rafiee et al.

(10) Patent No.: US 6,716,231 B1
(45) Date of Patent: Apr. 6, 2004

(54) DISTAL PROTECTION DEVICE

(76) Inventors: Nasser Rafiee, 39 Abbot St., Andover, MA (US) 01810; Jerry R. Brightbill, 26 Waldorf Rd., Newton, MA (US) 02461; David S. Brin, 84 Pine St., Danvers, MA (US) 01923; Timothy P. Collins, 124 Georgetown Rd., West Newbury, MA (US) 01985; Steven R. Dapolito, 129 Old Milford Rd., Brookline, NH (US) 03033; Barbara S. DeVaux, 116 Jericho Rd., Haverhill, MA (US) 01832; Nareak Douk, 905 Lakeview Ave., Lowell, MA (US) 01850; Albert H. Dunfee, 65 Pearson Dr., Byfield, MA (US) 01922; Heng Mao, 95 Tower Dr., Lowell, MA (US) 01854; Michael S. Noone, 114 Chase Rd., Londonderry, NH (US) 03053; Dennis L. Brooks, 9261 Piccadilly Cir., Windsor, CA (US) 95492; Robert D. Lashinski, 9519 Mill Station Rd., Sebastopol, CA (US) 95472

( * ) Notice: Subject to any disclaimer, the term of this patent is extended or adjusted under 35 U.S.C. 154(b) by 0 days.

(21) Appl. No.: 09/578,244

(22) Filed: May 24, 2000

Related U.S. Application Data

(63) Continuation-in-part of application No. 09/366,391, filed on Aug. 3, 1999, now Pat. No. 6,346,116.

(51) Int. Cl.[7] .............................................. A61M 29/00
(52) U.S. Cl. ..................................................... 606/200
(58) Field of Search ................................ 606/200, 113, 606/114, 127, 159

(56) References Cited

U.S. PATENT DOCUMENTS 4,425,908 A   1/1984   Simon
4,614,188 A * 9/1986   Bazell et al. .......... 604/101.05
4,723,549 A   2/1988   Wholey et al.
4,790,812 A  12/1988   Hawkins, Jr. et al.
4,873,978 A * 10/1989  Ginsburg .................... 606/198
4,926,858 A   5/1990   Gifford, III et al.
5,071,407 A  12/1991   Termin et al.
5,108,419 A * 4/1992   Reger et al. ................. 606/200
5,160,342 A  11/1992   Reger et al.
5,329,942 A   7/1994   Gunther et al.
5,421,832 A   6/1995   Lefebvre
5,549,626 A   8/1996   Miller et al.
5,695,519 A  12/1997   Summers et al.
5,814,064 A   9/1998   Daniel et al.
5,827,324 A * 10/1998  Cassell et al. ................. 604/22
5,910,154 A   6/1999   Tsugita et al.
5,911,734 A   6/1999   Tsugita et al.

(List continued on next page.)

FOREIGN PATENT DOCUMENTS

| FR | 2 768 326       | 3/1999  |          |
|----|-----------------|---------|----------|
| WO | WO 96/01591     | 1/1996  |          |
| WO | WO 98/33443     | 8/1998  |          |
| WO | WO 99/22673 A1  | 5/1999  |          |
| WO | WO 99/23976     | 5/1999  |          |
| WO | WO 9923976 A1 * | 5/1999  | ............ A61F/2/01 |
| WO | WO 00/16705 A1  | 3/2000  |          |
| WO | WO 00/44308 A2  | 8/2000  |          |
| WO | WO 00/67667 A1  | 11/2000 |          |
| WO | WO 00/67671 A1  | 11/2000 |          |
| WO | WO 01/08595 A1  | 2/2001  |          |
| WO | WO 01/21100 A1  | 3/2001  |          |

*Primary Examiner*—Kevin T. Truong
(74) *Attorney, Agent, or Firm*—James F. Crittenden

(57) ABSTRACT

The present invention is a distal protection device for use during a vascular treatment, such as angioplasty or atherectomy. A filter assembly located on the distal end of a delivery member is deployed distally of the vascular region to be treated to capture emboli released during and immediately after the procedure. The filter is then retracted to retain any captured emboli and then removed from the patient.

21 Claims, 5 Drawing Sheets

U.S. PATENT DOCUMENTS

| | | |
|---|---|---|
| 5,935,139 A | 8/1999 | Bates |
| 5,941,896 A * | 8/1999 | Kerr .......................... 606/192 |
| 5,972,019 A | 10/1999 | Engelson et al. |
| 6,001,118 A * | 12/1999 | Daniel et al. ............... 606/159 |
| 6,027,520 A * | 2/2000 | Tsugita et al. .............. 606/200 |
| 6,042,598 A | 3/2000 | Tsugita et al. |
| 6,059,814 A | 5/2000 | Ladd |
| 6,063,113 A | 5/2000 | Kavteladze et al. |
| 6,066,158 A | 5/2000 | Engelson et al. |
| 6,077,880 A * | 6/2000 | Castillo et al. ............. 523/105 |
| 6,096,053 A | 8/2000 | Bates |
| 6,123,715 A | 9/2000 | Amplatz |
| 6,142,987 A | 11/2000 | Tsugita |
| 6,152,946 A | 11/2000 | Broome et al. |
| 6,165,200 A | 12/2000 | Tsugita et al. |
| 6,171,327 B1 * | 1/2001 | Daniel et al. ............... 606/159 |
| 6,179,859 B1 * | 1/2001 | Bates et al. ................. 606/114 |
| 6,187,025 B1 * | 2/2001 | Machek ..................... 606/200 |
| 6,325,815 B1 * | 12/2001 | Kusleika et al. ............ 606/200 |

* cited by examiner

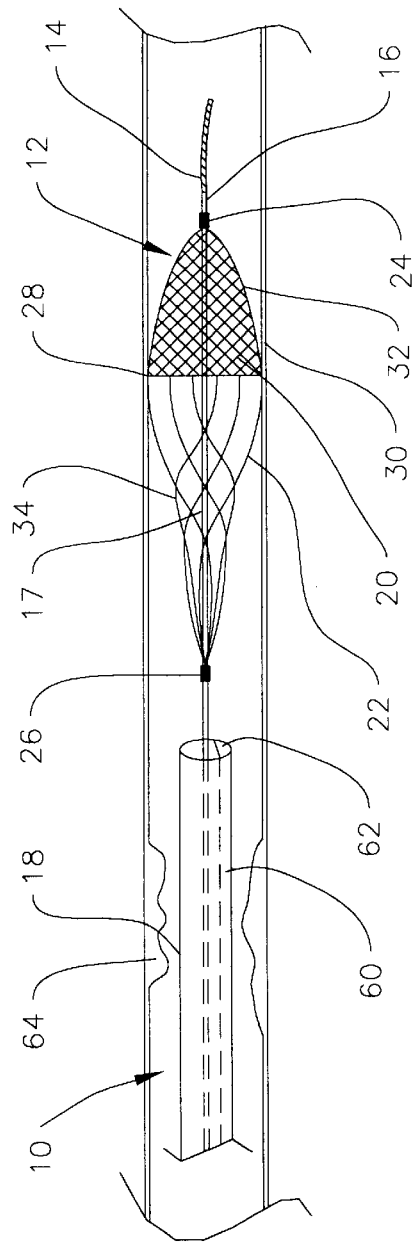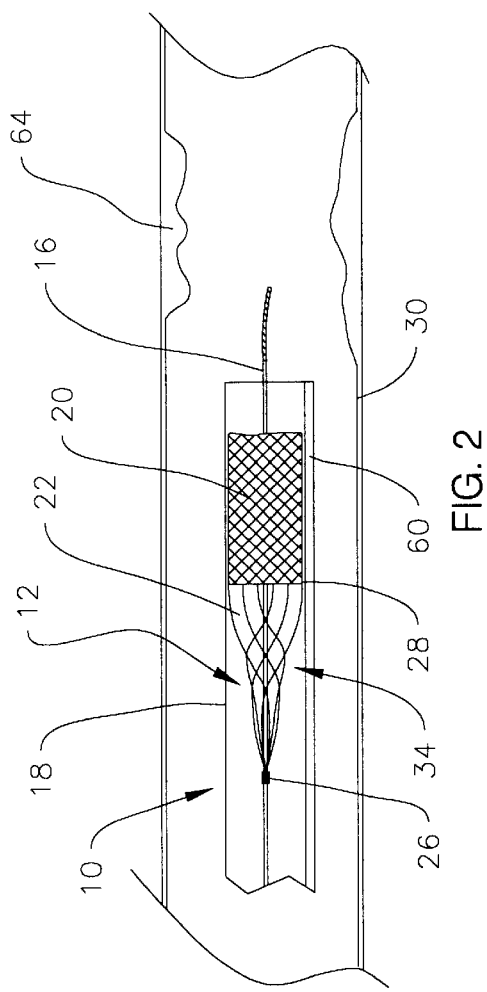

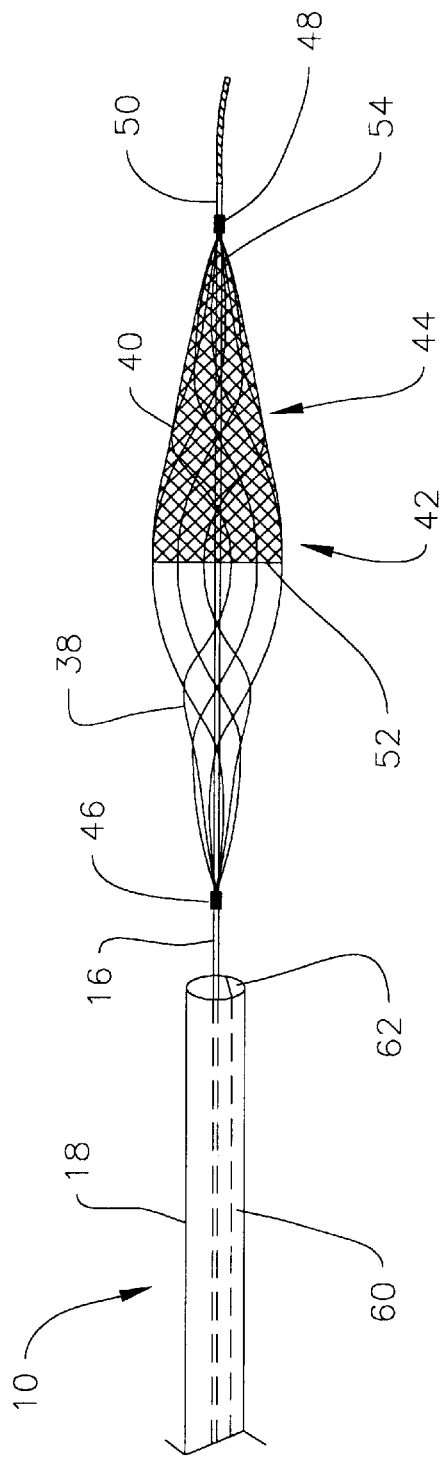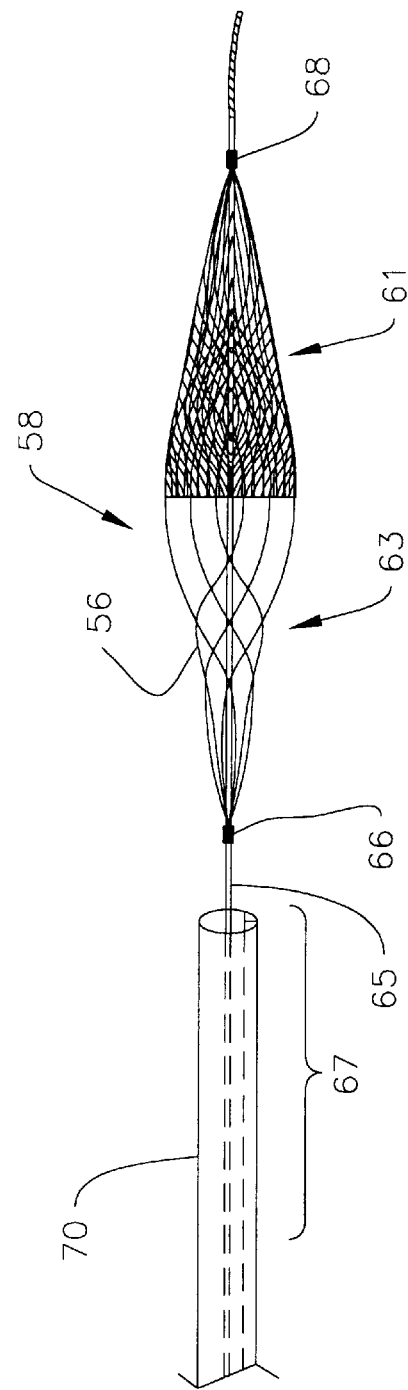
FIG. 3
FIG. 4

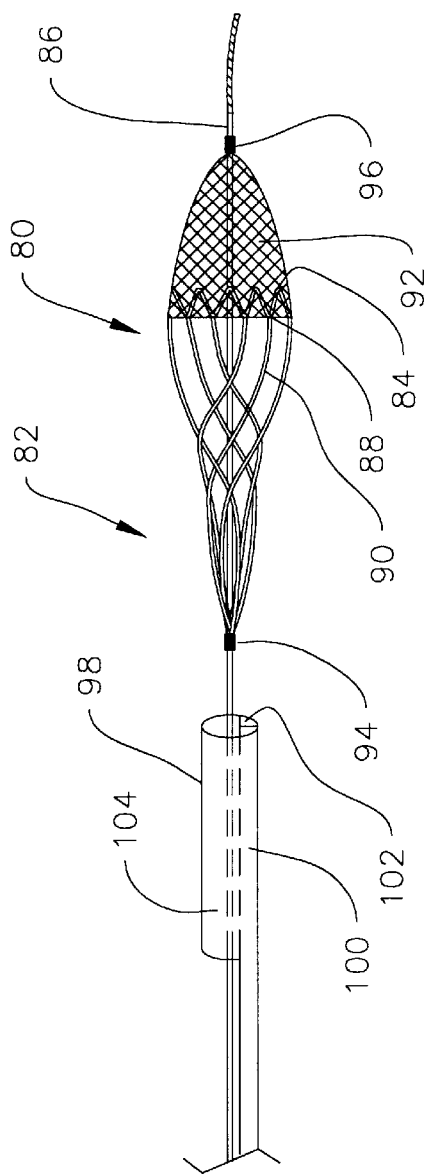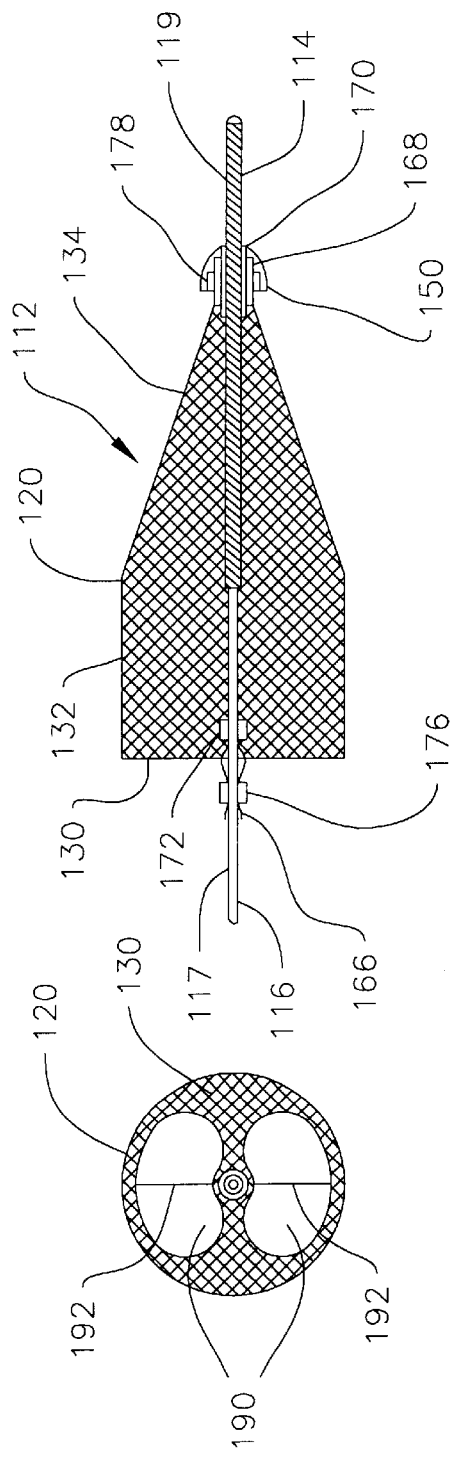

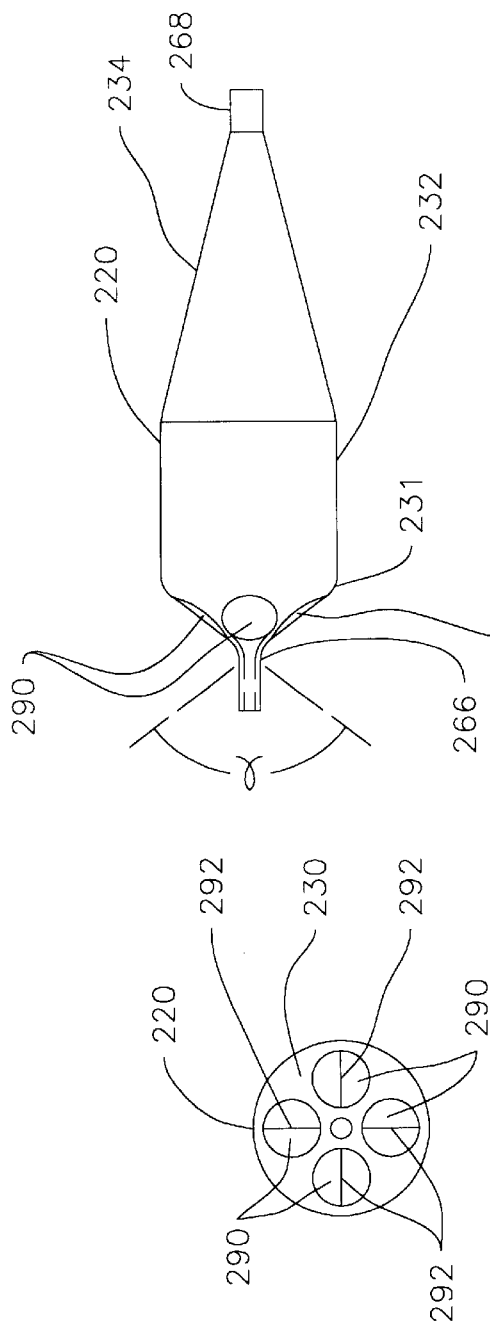
FIG. 8
FIG. 9
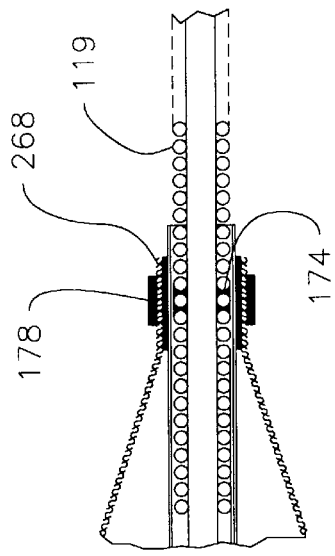
FIG. 10
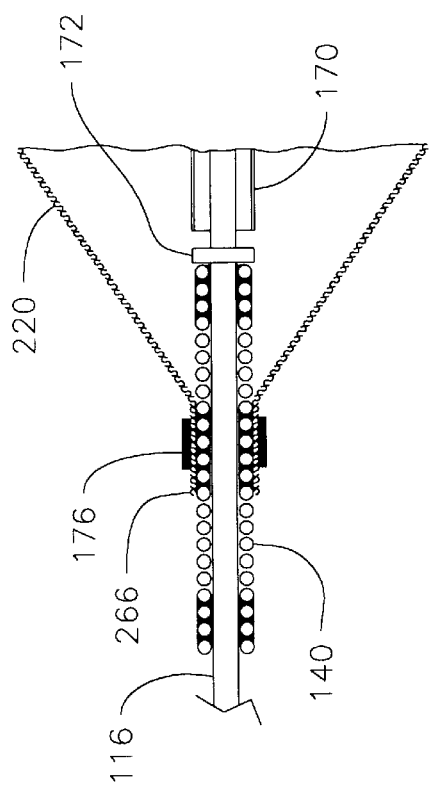

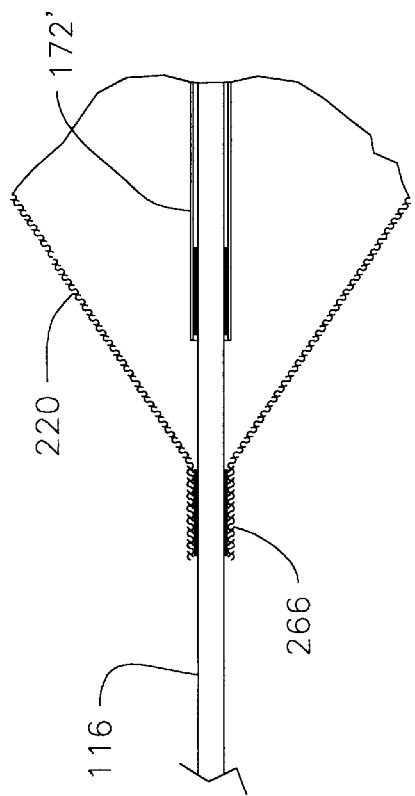
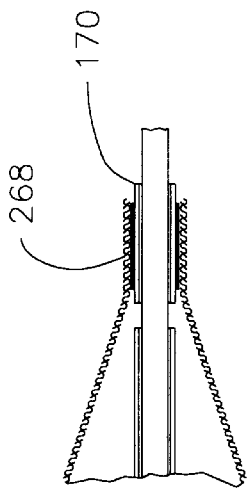
FIG. 11
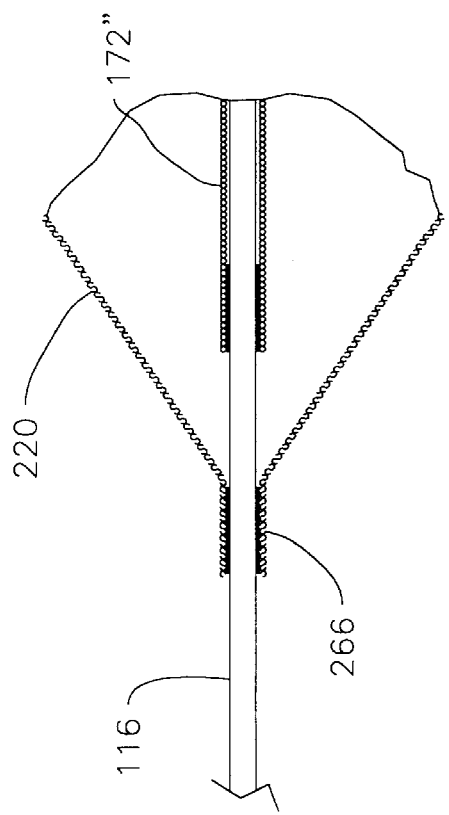
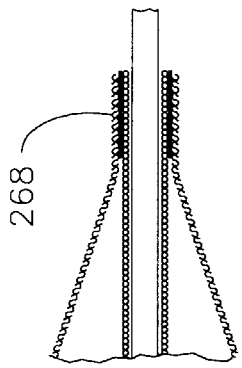
FIG. 12

DISTAL PROTECTION DEVICE

This application is a continuation-in-part of U.S. patent application Ser. No. 09/366,391 entitled "Distal Protection Device" and filed Aug. 3, 1999 now U.S. Pat. No. 6,346,116, the contents of which are hereby incorporated by reference.

FIELD OF THE INVENTION

The present invention relates generally to endovascular devices for capturing particulate. More particularly, the invention relates to a filter assembly located at the distal end of a delivery member to capture emboli in a blood vessel during a vascular procedure and then removing the captured emboli from the patient after completion of the procedure.

BACKGROUND OF THE INVENTION

A variety of treatments exist for compressing or removing athersclerotic plaque in blood vessels. The use of an angioplasty balloon catheter is common in the art as a minimally invasive treatment to enlarge a stenotic or diseased blood vessel. This treatment is known as percutaneous transluminal angioplasty, or PTA. To provide radial support to the treated vessel in order to prolong the positive effects of PTA, a stent may be implanted in conjunction with the procedure.

Removal of the entire thrombosis or a sufficient portion of the thrombosis to enlarge the stenotic or diseased blood vessel may be accomplished instead of a PTA procedure. Thrombectomy and atherectomy are well known minimally invasive procedures that mechanically cut or abrade the stenosis within the diseased portion of the vessel. Alternatively, ablation therapies use laser or RF signals to superheat or vaporize the thrombis within the vessel. Emboli loosened during such procedures are removed from the patient through the catheter.

During each of these procedures, there is a risk that emboli dislodged by the procedure will migrate through the circulatory system and cause clots and strokes. Thus, practitioners have approached prevention of escaped emboli through use of occlusion devices, filters, lysing and aspiration techniques. In atherectomy procedures, it is common to remove the cut or abraded material by suction though an aspiration lumen in the catheter or by capturing emboli in a filter or occlusion device positioned distal of the treatment area.

Prior art filters or occlusion devices are associated with either a catheter or guidewire and are positioned distal of the area to be treated. One prior art collapsible filter device includes a filter deployed by a balloon distal of a dilatation balloon on the distal end of a catheter. The filter consists of a filter material secured to resilient ribs. The ribs are mounted at the distal end of the catheter. A filter balloon is located between the catheter exterior and the ribs. Inflation of the filter balloon extends the ribs outward across the vessel to form a trap for fragments loosened by a dilatation balloon. When the filter balloon is deflated, the resilient ribs retract against the catheter to retain the fragments during withdrawal of the catheter.

Another prior art filter arrangement includes several filter elements fastened in spaced apart arrangement along the length of a flexible elongate member. This forms an open-mouthed tubular sock like arrangement to capture the emboli within. The filter is collapsed around the flexible elongate member by wrapping it spirally.

Yet another prior art filter includes a filter mounted on the distal portion of a hollow guidewire or tube. A core wire is used to open and close the filter. The filter has an expandable rim at its proximal end formed by the core wire. The filter is secured at the distal end to the guide wire.

Another prior art device has a filter made from a shape memory material. The device is deployed by moving the proximal end of the filter towards the distal end. It is collapsed and withdrawn by moving a sheath over the filter and then removing the sheath and filter.

A further prior art filter device discloses a compressible polymeric foam filter mounted on a shaft that is inserted over the guidewire. The filter is inserted collapsed within a housing which is removed to deploy the filter once in position. The filter is retracted by inserting a large bore catheter over the shaft and the filter and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be inserted onto the shaft and the filter is withdrawn into the shaft for removal from the patient.

Other known prior art filters are secured to the distal end of a guidewire with a tubular shaft. Stoppers are placed on the guidewire proximal and distal of the filter, allowing the filter to move axially and retract independently of the guidewire. A sheath is used to deploy and compress the filter.

One problem associated with known filter arrangements is that emboli may not be fully contained within the filter. Emboli can build up in the area just proximal of the filter, including any frame portion of the filter assembly. As the filter is closed, emboli not fully contained in the filter can escape around the filter into the circulatory system and cause potentially life threatening strokes. While the blood flow is inhibited when an occlusion device is used during the procedure, emboli can escape as the occlusion device is withdrawn from the treatment area.

Therefore, what is needed is a filter arrangement that addresses the problem of emboli not fully contained in the filter assembly or captured by an occlusion device. Furthermore, there is a need for a filter assembly that is adaptable for delivery with standard PTA balloon or stent delivery catheters. Additionally there is a need for a filter arrangement that is secure by being mounted at its distal and proximal ends to the delivery member ensuring proper placement of the filter throughout deployment, capture of the emboli and subsequent removal of the filter and captured emboli.

SUMMARY OF THE INVENTION

The present invention is a distal protection device for use in vascular procedures. The distal protection device includes a filter assembly adjacent the distal end of a delivery member used in the procedure. The proximal and distal ends of the filter assembly are fixed to the delivery member such that the ends cannot move longitudinally along the delivery member, but may rotate independently of the delivery member core. The filter assembly includes an expandable frame with a distal portion acting as the emboli filter. The emboli filter is sized sufficiently to expand and cover the cross sectional area of the vessel just distal of the intended treatment area.

The filter assembly may have a variety of configurations. In one embodiment, the frame consists only of the proximal portion of the filter assembly, with the distal half formed from filter material. The frame can have a braided configuration or consist of a sinusoidal ring element adjacent the filter material with helical segments extending from the sinusoidal ring to the delivery member. In another embodiment, the frame forms a basket arrangement and includes the filter material in the disial half of the basket. Such a frame can be configured with a tighter braid on the distal end, thus obviating the need for a filter material.

The filter assembly further includes a moveable sheath for positioning the emboli filter between an expanded position and a collapsed position. The sheath extends over the frame, collapsing the frame and filter of the assembly as they are drawn into the sheath. Likewise, when the frame and filter are removed from the sheath, they will expand so the filter will cover the cross sectional area of the vessel distal of the treatment area.

Alternative embodiments of the filter assembly can include an aspiration lumen extending through the sheath or a flushing lumen extending through the sheath. This allows large emboli to be lysed or aspirated prior to retracting the filter and removing it from the patient.

Another alternative embodiment of the filter assembly has the proximal end of the filter longitudinally fixed to the delivery member, the distal end of the filter being slidingly attached to the member. When a sheath is passed over the filter to compress it for delivery or retrieval, the distal end of the filter slides distally on the delivery member, extending the length of the filter. The filter of this embodiment may also include a frame that is densely braided from end-to-end to form a basket with fine pores. The filter also has large inlet openings that are formed in the proximal end after braiding. The deployed shape of this filter embodiment is generally that of a teardrop, the proximal end having a generally obtuse cone and the distal end having a generally acute cone. A cylindrical well defines the filter body between the proximal and distal cones.

The sheath is configured to be used with either a rapid exchange arrangement or an over-the-wire arrangement as well known to those skilled in the art.

BRIEF DESCRIPTION OF DRAWINGS

For a more complete understanding of the features, aspects, and advantages of the present invention, reference is now made to the following description, appended claims, and accompanying drawings wherein:

FIG. 1 is a side view of a catheter and delivery member incorporating a distal protection device of the present invention, with the distal protection device shown deployed in a vessel;

FIG. 2 is a side view taken of the distal portion of a catheter and delivery member incorporating a distal protection device of the present invention, with the distal protection device shown constrained in the catheter, which is shown in section;

FIG. 3 is a side view of a second filter arrangement of the present invention shown deployed;

FIG. 4 is a side view of a third filter arrangement of the present invention shown deployed;

FIG. 5 is a side view of a rapid exchange styled delivery sheath and a fourth filter arrangement of the present invention;

FIG. 6 is a side view of a fifth filter arrangement of the present invention wherein the filter is shown in longitudinal section;

FIG. 7 is view of the proximal end of the fifth filter arrangement shown in FIG. 6;

FIG. 8 is a side view of a sixth filter of the present invention;

FIG. 9 is a view of the proximal end of the sixth filter shown in FIG. 8;

FIG. 10 is a broken longitudinal section of a seventh filter arrangement of the present invention;

FIG. 11 is a broken longitudinal section of an eighth filter arrangement of the present invention; and FIG. 12 is a broken longitudinal section of an ninth filter arrangement of the present invention.

DETAILED DESCRIPTION OF THE PREFERRED EMBODIMENTS

The present invention is a distal protection device, designated 10 in FIG. 1 for use in minimally invasive procedures, such as vascular procedures or other procedures where the practitioner desires to capture material that may be dislodged during the procedure. The distal protection device 10 includes a filter assembly 12 located adjacent the distal end 14 of a delivery member 16. In this preferred embodiment delivery member 16 can be a modified guidewire assembly, hereinafter referred to as either "delivery member," "guidewire," or "core wire." Filter assembly 12 is delivered, deployed and retrieved by a sheath 18 arranged to be slid over filter assembly 12. When the distal protection device 10 is in a constrained position, filter assembly 12 is collapsed within sheath 18 as shown in FIG. 2. When filter assembly 12 is deployed, sheath 18 is withdrawn releasing filter assembly 12 as shown in FIG. 1.

Filter assembly 12 includes a filter 20 and a frame 22 and is secured to delivery member 16 at its distal portion 24 and proximal portion 26. Preferably, the filter assembly ends 24 and 26 are fixed in the longitudinal position, but are capable of rotational movement independent of the guidewire core 17 while maintaining the longitudinal position. Filter 20 is formed from a suitable mesh or porous material that will filter emboli from blood while permitting sufficient perfusion therethrough. For example, a porous filter can be formed from urethane material by adding salt, sugar or other granular particles during the casting of the urethane filter. Following the cutting and curing processes, these granular particles are dissolved forming a porous urethane filter as well known to those skilled in the art. Other suitable filter materials may include nylon, ePTFE, teflon, kevlar and the like having an appropriate porous construction to filter emboli from blood passing through the filter.

Filter assembly 12 is positioned concentric with delivery member 16. Filter 20 is sized such that when it is fully deployed, as in FIG. 1, its proximal edge 28 will contact the inner surface of the blood vessel wall 30. The inner surface contact is preferably maintained over the entire cross section to prevent any emboli from escaping past filter 20. Filter 20 is preferably secured at its proximal edge 28 to frame 22 and at its distal portion 32 to the delivery member 16.

Frame 22 of filter assembly 12 is an expandable frame made from a shape memory material, such as nitinol, a suitable polymer, stainless steel or other suitable materials. Several struts, designated generally as 34, extend from the delivery member 16 at proximal connection 26 to proximal edge 28 of filter 20, to form frame 22, as seen in FIGS. 1 and 2.

Alternatively, struts 38 may extend around filter 40 forming a basket frame 42 with filter 40 on at least the distal portion 44 of basket frame 42 as shown in FIG. 3. In such an arrangement, basket frame 42 is secured preferably at its proximal end 46 and distal end 48 to guidewire 50. As with the embodiment of FIG. 1, basket frame 42 is fixed on the guidewire at a longitudinal position where it is capable of rotational movement independent of guidewire 50. Filter 40 is secured at its proximal end 52 to basket frame 42 and at its distal end 54 to basket frame 42. Filter 40 can be secured to the struts 38 on the distal portion 44 of basket frame 42. Alternatively, filter 40 may be formed on basket frame 42 by dip coating select portions of basket frame 42 with a suitable material such as urethane and treating the material to form the desired porous structure on distal portion 44.

A variety of strut configurations are suitable including the braid configuration shown in FIG. 1. Struts 56 of filter assembly basket 58 shown in FIG. 4 have a dense braid on distal portion 61 that transitions to a less dense braid on proximal portion 63. Filter material may be located on distal portion 61 either by having a separate filter material or by dip coating selected portions of the basket 58 as discussed above with respect to the embodiment shown in FIG. 3. Alternatively, the braid of the struts 56 may be sufficiently dense on distal portion 61 to act as a porous filter thus obviating the need for a separate filter material or selective dip coating of basket 58. Filter assembly basket 58 is fixed to the guidewire 65 at its proximal end 66 and distal end 68. Again, filter assembly basket 58 is preferably fixed at a longitudinal position on guidewire 65 where it is capable of rotational movement independent of the guidewire core. A sheath 70 is used to deploy filter assembly basket 58.

Filter assembly 80 shown in FIG. 5 is similar to the filter arrangement of FIG. 1. Frame 82 consists of a distal ring 84 formed from a sinusoidal element. Extending from ring 84 to the guide wire 86 are helical members 90. For example, one such member 90 extends between apex 88 of ring 84 and guidewire 86. Distal end 96 of filter 92 is secured to guidewire 86.

Sheath 98 includes an aspiration lumen 100 and lysing lumen 102. While two lumens are shown, as known to those skilled in the art, only an aspiration or lysing lumen may be incorporated in sheath 98. Sheath 98 also includes a short guidewire lumen 104 resulting in a sheath configured as a rapid exchange sheath. A preferred construction for either of sheaths 18 or 98, as shown in FIG. 4, is to incorporate a more radiopaque distal region 67 into the shaft. Distal region 67 is more radiopaque than the remainder of the sheath because it contains a larger amount of a radiopacifying agent. The sheath preferably contains 30% bismuth subcarbonate, and region 67 contains 80% tungsten powder. A preferred polymer material for the sheaths is a 55D polyether block amide such as PEBAX® by Elf Atochem North America, Inc. of Philadelphia, Pa. Region 67 can simply be joined to the remainder of sheath 18 by butt joining techniques well known to those skilled in the art. Because distal region 67 contains a radiopacifying agent that is both higher in quantity and more dense than the agent in the remainder of the sheath, region 67 is also stiffer than the remainder of the sheath.

FIG. 6 shows a fifth filter assembly embodiment, which may be used with deployment and recovery catheters such as sheath 18 or sheath 98. Either sheath 18 or sheath 98 can be used to transform filter assembly 112 between its deployed configuration shown in FIG. 6 and a collapsed configuration similar to that of filter assembly 12, shown in FIG. 2.

Filter assembly 112 has a filter 120 shaped to have a cylindrical central well 132, a distal cone 134, and proximal surface 130. The cylindrical shape of the central well 132 provides greater surface area for contacting the vessel wall. With greater contact area, filter assembly 112 will have more secure apposition against the vessel wall during treatment. Cylindrical well 132 can also provide a larger inner volume for retention of emboli.

Because the filters of such distal protection devices are intended to be placed downstream of, or distal to, the treatment area of the vasculature, it is preferred to have the filter as short as possible. Having short filter length enables treatment in the middle or even distal area of a vessel, such as a coronary artery, while still having enough room to place the filter downstream of the treatment site. The proximal surface 130 is a flat plane that is perpendicular to cylindrical central well 132. The flat shape of proximal surface 130 adds negligible axial length to the filter 120, especially in comparison to proximal portion 66 of filter assembly basket 58 in FIG. 4. Considering proximal surface 130 as a cone, as shown in other embodiments, it has an included angle of 180°.

In filter assembly 112, filter 120 is mounted adjacent the distal end 114 of a delivery member, or guidewire 116, which preferably has a slender shaft 117 with a surrounding coil spring 119 at distal end 114. Preferably, coil spring 119 ends proximally within filter 120. Proximal end 166 and distal end 168 of filter 120 are attached to guidewire 116. Proximal end 166 is preferably fixed to guidewire 116 using solder, braze or adhesives. Alternatively, as shown in FIG. 10, proximal end 266 can be attached to guidewire 116 such that a limited amount of rotation is permitted between guidewire 116 and filter 120. Helical member 140 loosely surrounds guidewire 116 with its proximial and distal ends secured thereto, and extends proximal and distal to filter proximal end 266. Proximal end 266 is secured between the proximal and distal ends of member 140, without this bond attaching to underlying guidewire 116, such that the full length of member 140, except for its ends, is capable of limited rotation with respect to guidewire 116.

Distal end 168 is preferably mounted to tubular slider 170, which provides a sliding mount over distal end 114 of guidewire 116. Slider 170 may be formed from any suitable plastic or metallic material, preferably a thin-walled polyimide thermoset polymer. Adhesive is preferably used to bond distal end 168 to slider 170. Preferably, proximal and distal radiopaque marker bands 176 and 178, respectively, are mounted over proximal end 166 and distal end 168. Bullet-nose tip 150 is formed over slider 170, distal end 168 and marker band 178. Tip 150 may be a combination of molded pieces and an adhesive fillet, and is tapered distally to provide smooth passage through body passageways. The outer diameter of tip 150 approximately matches the outer diameter of sheaths 18 or 98 such that when either sheath is slid over filter 112, it fits against the proximal side of tip 150. Optionally, a third radiopaque marker band 174 may be incorporated into guidewire 116, as shown in FIG. 10. When viewed on fluoroscopy during the medical procedure, the coaxial alignment of bands 178 and 174 will indicate that filter 220 has been fully deployed. During the compressed configuration, filter 220 will be elongated such that band 178 will appear distally of band 174 on fluoroscopy.

Stop 172 can be a short piece of tubing bonded to guidewire 116 between filter ends 166 and 168. Stop 172 offers a sliding stop or reserve connection to prevent filter 120 from detaching from guidewire 116 in the event of a bond failure between proximal end 166 and guidewire 116. When sheath 18 is advanced against filters 120 or 220 to compress them, there may be a tendency for proximal cones 130 or 230 to invert into the interiors of the filters. To prevent such inversions, an extended stop 172', as shown in FIG. 11, nearly contacts distal end 268 or slider 170. Proximal cone inversions, or excessive shortening of filter 220 are prevented during various manipulations of assembly 112 by keeping distal end 268 and proximal end 266 apart by a minimum distance.

In another embodiment, stop 172" is formed by a coil spring, as shown in FIG. 12. Stop 172" has a proximal end secured to core wire 116 and a distal end secured to distal end 266. In the deployed configuration, the coils of stop 172" are stacked together, preventing further shortening of filter 220. During compression of filter 220, ends 266 and 268 separate and stop 172" elongates, increasing tension force therein as the coils are separated. This tension force may be useful to deploy stent 220 upon release from sheath 18 or sheath 98. Having an internal deployment force from stop 172" makes it easier to fabricate filter 220 from materials other than shape memory alloys such as NiTi (nitinol), because filter 220 does not need to provide its own deployment force.

Filter assembly 112 is similar to filter assembly basket 58 shown in FIG. 4, wherein the struts 56 alone make the filter basket by using a densely braided structure. Filter 120 is formed with a generally constant pitch braid, preferably providing a uniform pore size of approximately 75–125 microns, such that no additional filter material is necessary.

Proximal surface 130 includes inlet ports 190, as shown in FIG. 7. Ports 190 are formed after filter 120 has been braided by inserting metal shaping mandrels into the proximal surface and applying a heat treatment to the braid of filter 120. Ports 190 are best described when viewed from the proximal end of the filter assembly 112 because this view shows the shapes of the mandrels used to make inlet ports 190, even when the proximal surface of the filter is other than flat, as in the sixth embodiment of the invention, which will be discussed below. Ports 190 provide filter inlet openings that are substantially larger than the size of the pores in filter 120. Ports 190 may have a variety of preferably rounded, symmetrical shapes, each having an axis 192 in-plane with a radius of the cylindrical central well 132. To efficiently gather particulate matter, ports 190 should also expose as much of the proximal surface 130 as possible, especially near its perimeter, without compromising the structural integrity of filter 120. Such ports 190 will have axes 192 as long as possible, such as approximately 90% of the difference between the radius of central well 132 and the radius of proximal end 166. FIG. 7 shows two large kidney-shaped ports 190 formed in the flat proximal surface 130 of the fifth filter embodiment. Alternative structures may include a larger number of smaller ports 190, thus providing more braid material therebetween to connect cylindrical well 132 to proximal end 166.

A sixth embodiment of the filter is shown in FIGS. 8, 9 and 10. Either of sheaths 18 or 98 can be used to transform filter 220 between its generally teardrop shaped, deployed configuration shown in FIG. 8 and a collapsed configuration similar to that of filter 20, shown in FIG. 2. Filter 220 is shaped to have a cylindrical central well 232, a distal cone 234, a proximal surface 230, and proximal and distal ends 266 and 268, respectively. Filter 220 is similar to filter 120 except that the proximal surface 230 is conical instead of flat, and rounded shoulder 231 forms the transition from surface 230 to cylindrical central well 232. As viewed from the proximal end, four circular inlet ports 290 are equally spaced around proximal surface 230, each port having an axis 292 in-plane with a radius of the central well 232. The included cone angle $\alpha$ of proximal surface 230 is preferably more than 90°, most preferably about 100°. The combination of conical surface 230 and rounded shoulder 231 have shown a reduced likelihood to scrape the vessel wall and improved particulate collection efficiency.

The deployment of filter assembly 12 will now be described, although the procedure explained is equally applicable to any of the filter assembly embodiments disclosed herein. The deployment mechanism includes sheath 18 that is sized to travel over delivery member 16 and receive the filter assembly 12 therein as shown in FIG. 2. Sheath 18 may incorporate an aspiration lumen 60. Additionally, sheath 18 may incorporate a flushing lumen 62 (FIG. 1) to enable the practitioner to flush the filter assembly with a lysing agent prior to and during the procedure to remove emboli lodged on the struts. The sheath is constructed for use as either an over-the-wire system shown with sheath 18 in FIG. 1, or a rapid exchange system, shown with sheath 98 in FIG. 5.

In operation, sheath 18 is extended over delivery member 16 until it fully covers filter assembly 12 as shown in FIG. 2. Sheath 18, filter assembly 12 and delivery member 16 are then inserted into the patient and routed to the area to be treated, designated as 64 in FIG. 1. Filter assembly 12 and sheath 18 are positioned past the area 64 to be treated. Sheath 18 is then withdrawn, releasing struts 34 of filter assembly 12. As struts 34 resume their unrestrained position, filter 20 expands to fill the cross sectional area of the vessel. Sheath 18 may then be completely withdrawn from delivery member 16 and then an appropriate second device, such as a treatment catheter, can be routed over delivery member 16 to the treatment area.

During and after the treatment such as, an angioplasty, atherectomy or the like procedure, emboli can be dislodged. The emboli will travel downstream and be captured by filter 20. The treatment catheter is removed after the procedure and sheath 18 is loaded on delivery member 16 and delivered to the treatment area 64. Prior to collapsing the filter assembly 12, the practitioner can aspirate the area to remove any loose emboli that may not be sufficiently captured in filter 20. For example, emboli may be lodged on struts 34 proximal of filter 20. When filter 20 is collapsed, these emboli may escape into the blood stream. Thus, the particles should be removed. Furthermore, the practitioner may choose to flush the area with a lysing agent to reduce the size of the emboli within filter 20 or struts 34 prior to recapturing the filter.

The practitioner then extends sheath 18 over filter assembly 12 compressing filter 20 and the captured emboli within sheath 18. Sheath 18, filter assembly 12 and delivery member 16 can then be removed from the patient. When sheath 18 is advanced against filters 120 or 220 to compress them, there may be a tendency for proximal cones 130 or 230 to invert into the interiors of the filters. To prevent this inversion, slider 170 may extend proximally from distal end 168 into the interior of filter 220 as shown in FIG. 10. If the filter tends to shorten during compression, slider 170 will abut against another member such as proximal end 266, or safety stop 172 to limit this shortening and prevent the inversion of the proximal cone.

The foregoing embodiments and examples are illustrative and are in no way intended to limit the scope of the claims set forth herein. For example, the filter material can be a nylon or PET film that has holes poked therethrough. The filter can be mounted onto a delivery member such as a catheter or integral with a dilatation balloon for advancing across a tight stenosis. These and other alternatives are within the scope of the invention.

We claim:

1. A distal protection device comprising:
   a delivery member having a proximal end a distal end;
   a filter assembly having proximal and distal ends coupled adjacent the distal end of the delivery member, the filter assembly having pores and being transformable between a deployed configuration and a collapsed configuration, the deployed configuration having:
   a cylindrical well;
   a distal cone extending from the cylindrical well to the filter assembly distal end and comprising an acute included angle;
   a proximal cone extending from the cylindrical well to the filter assembly proximal end and comprising an included angle that is generally obtuse, the proximal cone having a plurality of inlet openings that are substantially larger than the pores; and
   a rounded shoulder formed between the cylindrical well and the proximal cone.

2. The distal protection device of claim 1 further comprising a sheath that is selectively moveable over the delivery member for transforming the filter assembly between the deployed configuration and the collapsed configuration.

3. The distal protection device of claim 1 wherein the included angle of the proximal cone is 180°.

4. The distal protection device of claim 1 wherein the shape of the deployed configuration of the filter assembly is generally that of a teardrop.

5. The distal protection device of claim 1 wherein at least one inlet opening has a rounded symmetrical shape having an axis in-plane with a radius of the cylindrical well.

6. The distal protection device of claim 5 wherein the shape of the at least one inlet opening is a circle when viewed from the proximal end of the filter assembly.

7. The distal protection device of claim 5 wherein the axis of the at least one inlet opening extends substantially from the rounded shoulder to the proximal end of the filter assembly.

8. The distal protection device of claim 7 wherein the at least one inlet opening comprises four inlet openings equally spaced about the surface of the proximal cone.

9. A vascular filter apparatus comprising:
   a core wire having proximal and distal ends;
   a filter arranged around the core wire and having:
   proximal and distal ends coupled to the core wire adjacent the core wire distal end;
   a dense braid from end-to-end, forming fine pores;
   a deployed configuration and a collapsed configuration, the deployed configuration having:
   a cylindrical central well;
   a distal cone extending from the central well to the filter distal end and comprising an acute included angle;
   a proximal cone extending from the central well to the filter proximal end and comprising an obtuse included angle, the proximal cone including a plurality of inlet openings that are substantially larger than the fine pores; and
   a rounded shoulder formed between the central well and the proximal cone.

10. The vascular filter apparatus of claim 9, further comprising a sheath slidably mounted on the core wire and having proximal and distal sections, the distal section of the sheath having a lumen of sufficient diameter to contain at least a proximal portion of the collapsed configuration of the filter.

11. The vascular filter apparatus of claim 10, further comprising the sheath having the distal section being radiopaque.

12. The vascular filter apparatus of claim 10, further comprising the sheath having the distal section being more radiopaque than the proximal section.

13. The vascular filter apparatus of claim 10, further comprising the proximal section containing a first radiopaque agent, the distal section containing a second radiopaque agent, the distal section being more radiopaque than the proximal section.

14. The vascular filter apparatus of claim 9, further comprising a first radiopaque band affixed to the proximal end of the filter and a second radiopaque band affixed to the distal end of the filter.

15. The vascular filter apparatus of claim 14, wherein the filter proximal end is longitudinally fixed to the core wire and the filter distal end is slidingly coupled to the core wire, the filter apparatus further comprising a third radiopaque band affixed to the core wire such that, when the filter is in the deployed configuration, the second band aligns with the third band.

16. The distal protection device of claim 9 wherein at least one inlet opening has a rounded symmetrical shape having an axis in-plane with a radius of the cylindrical well.

17. The distal protection device of claim 16 wherein the shape of the at least one inlet opening is a circle when viewed from the proximal end of the filter assembly.

18. The distal protection device of claim 16 wherein the axis of the at least one inlet opening extends substantially from the rounded shoulder to the proximal end of the filter assembly.

19. The distal protection device of claim 18 wherein the at least one inlet opening comprises four inlet openings equally spaced about the surface of the proximal cone.

20. A vascular filter apparatus comprising:
   a core wire having proximal and distal ends;
   a filter arranged around the core wire, the filter having a proximal end, a distal end, a deployed configuration and a collapsed configuration, the deployed configuration having a distal cone, a proximal cone, and a length, the proximal end of the filter being attached to the core wire; and
   a tubular slider being sliding disposed around the core wire, the filter distal end being secured about the slider and, the slider extending proximally from the filter distal end through the deployed length of the filter to a location adjacent the filter proximal end.

21. A vascular filter apparatus comprising:
   a core wire having proximal and distal ends;
   a filter arranged around the core wire, the filter having proximal and distal ends, the distal end of the filter having a slidable attachment to the core wire adjacent its distal end; and
   a helical member having proximal and distal ends that are secured to the core wire received there through, the proximal end of the filter being secured to the helical member between the proximal and distal ends thereof such that the core wire is capable of limited rotation with respect to the filter.

* * * * *